US009034379B2

(12) United States Patent
Freier

(10) Patent No.: US 9,034,379 B2
(45) Date of Patent: *May 19, 2015

(54) PROCESSING OF ACYLCHITOSAN HYDROGELS

(71) Applicant: Thomas Freier, Mainz (DE)

(72) Inventor: Thomas Freier, Mainz (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/850,568

(22) Filed: Mar. 26, 2013

(65) Prior Publication Data

US 2013/0276669 A1 Oct. 24, 2013

Related U.S. Application Data

(62) Division of application No. 12/067,727, filed as application No. PCT/EP2006/009830 on Oct. 11, 2006, now Pat. No. 8,414,925.

(60) Provisional application No. 60/725,575, filed on Oct. 12, 2005, provisional application No. 60/725,610, filed on Oct. 12, 2005.

(51) Int. Cl.
| | |
|---|---|
| *A61L 31/04* | (2006.01) |
| *A61K 9/16* | (2006.01) |
| *A61K 9/00* | (2006.01) |

(Continued)

(52) U.S. Cl.
CPC ............ *A61L 31/042* (2013.01); *A61K 9/1652* (2013.01); *A61K 9/0024* (2013.01); *A61K 9/0092* (2013.01); *A61K 47/36* (2013.01); *A61L 27/20* (2013.01); *A61L 27/34* (2013.01); *A61L 27/50* (2013.01); *A61L 27/52* (2013.01); *A61L 29/043* (2013.01); *A61L 29/085* (2013.01); *A61L 29/14* (2013.01); *A61L 29/145* (2013.01); *A61L 31/10* (2013.01); *A61L 31/14* (2013.01); *A61L 31/145* (2013.01); *C08B 37/003* (2013.01); *C08J 3/075* (2013.01);

(Continued)

(58) Field of Classification Search
CPC .... A61K 47/36; A61K 9/1652; A61K 9/0024
See application file for complete search history.

(56) References Cited

U.S. PATENT DOCUMENTS

| | | | |
|---|---|---|---|
| 2,040,880 | A | 5/1936 | Rigby |
| 3,988,411 | A | 10/1976 | Capozza |

(Continued)

FOREIGN PATENT DOCUMENTS

| | | |
|---|---|---|
| CN | 1385217 A | 12/2002 |
| DE | 19724869 A1 | 12/1998 |

(Continued)

OTHER PUBLICATIONS

"Shaping Processes for Plastics", Wiley & Sons, Inc, MP Groover, "Fundamentals of Modern Manufacturing 2/e", 2002.*

(Continued)

*Primary Examiner* — Carlos Azpuru
(74) *Attorney, Agent, or Firm* — Harris Beach PLLC

(57) ABSTRACT

An article containing N-acylchitosan is manufactured by a process comprising the steps of providing a mixture containing chitosan and/or N-acylchitosan, and extruding the mixture to form an N-acylchitosan hydrogel. Alternatively, the process comprising the steps of providing a chitosan and/or N-acylchitosan hydrogel, and extruding the hydrogel. An article with a memorized shape is formed by fixing the N-acylchitosan hydrogel in a desired shape, and at least partially drying the fixed hydrogel. A patient is treated by injecting the N-acylchitosan hydrogel.

20 Claims, 6 Drawing Sheets

(51) Int. Cl.
  A61L 27/20    (2006.01)
  A61L 27/34    (2006.01)
  A61L 27/50    (2006.01)
  A61L 27/52    (2006.01)
  A61L 29/04    (2006.01)
  A61L 29/08    (2006.01)
  A61L 29/14    (2006.01)
  A61L 31/10    (2006.01)
  A61L 31/14    (2006.01)
  C08B 37/08    (2006.01)
  C08J 3/075    (2006.01)
  C08L 5/08     (2006.01)
  D01D 5/06     (2006.01)
  D01F 9/00     (2006.01)
  A61K 47/36    (2006.01)

(52) U.S. Cl.
  CPC ............... *C08J 2305/08* (2013.01); *C08L 5/08* (2013.01); *D01D 5/06* (2013.01); *D01F 9/00* (2013.01)

(56) References Cited

U.S. PATENT DOCUMENTS

| | | | |
|---|---|---|---|
| 4,059,457 | A | 11/1977 | Austin |
| 4,932,404 | A | 6/1990 | Kifune et al. |
| 5,900,479 | A | 5/1999 | Glasser et al. |
| 6,368,356 | B1 | 4/2002 | Zhong et al. |

FOREIGN PATENT DOCUMENTS

| | | | |
|---|---|---|---|
| DE | 19829663 | A1 | 10/1999 |
| EP | 0021750 | A1 | 1/1981 |
| EP | 0271887 | A2 | 6/1988 |
| WO | WO-0050103 | A1 | 8/2000 |
| WO | WO-03042250 | A1 | 5/2003 |

OTHER PUBLICATIONS

Hirano, Shigehiro et al. Chitin xanthate and some xanthate ester derivatives 1994 Carbohydrate Research 256 (pp. 331-336).

International Preliminary Report on Patentability for PCT/EP06/09830 issued Apr. 15, 2008 (8 pgs.).

International Search Report and Written Opinion of the International Searching Authority for PCT/EP06/09830 mailed Dec. 20, 2007 (12 pgs.).

European Examination Report for European Application No. 06 806 193.6 dated May 6, 2010 (5 pgs.).

Yang, Yumin et al., "Medical-use nerve of chitosan and its production" Aug. 12, 2004 Abstract STN Database Accession No. 141: 128888 (1 pg.).

Hirano et al., "Fiber Preparation of N-Acetylchitosan and its cellulose blend by spinning their aqueous xanthate solutions," 1998 Carbohydrate Polymers 37 (pp. 311-313).

Gerentes et al., "Study of a chitin-based gel as injectable material in periodontal surgery," 2002 Biomaterials 23 (pp. 1295-1302).

Freier et al., "Chitin-based tubes for tissue engineering in the nervous system," 2005 Biomaterials 26 (pp. 4624-4632).

Knaul et al., "Crosslinking of Chitosan Fibers with Dialdehydes: Proposal of a New Reaction Mechanism," 1999 Journal of Polymer Science, Part B: Polymer Physics, vol. 37 (pp. 1079-1094).

Rathke et al., "Review of Chitin and Chitosan as Fiber and Film Formers," 1994 J.M.S. Rev. Macromol. Chem. Phys. C34(C) (pp. 375-437).

Shigemasa et al., "Applications of Chitin and Chitosan for Biomaterials," Dec. 1995 Biotech Genetic Eng. Rev., vol. 13 (pp. 383-420).

Kumar, "A review of chitin and chitosan applications," 2000 Reactive & Functional Polymers 46 (pp. 1-27).

Singh et al., "Biomedical Applications of Chitin, Chitosan and Their Derivatives," 2000 J.M.S. Rev. Macromol. Chem. Phys., C40(1) (pp. 69-83).

* cited by examiner

PROCESSING OF ACYLCHITOSAN HYDROGELS

CROSS-REFERENCE TO RELATED APPLICATIONS

This application is a divisional application of U.S. national stage application Ser. No. 12/067,727 filed May 28, 2008, which is a National Stage application of PCT/EP2006/009830, filed Oct. 11, 2006, which claims priority to U.S. Provisional Application Nos. 60/725,575, filed Oct. 12, 2005 and 60/725,610, filed Oct. 12, 2005. The entire contents of each of the aforementioned applications are incorporated herein by reference.

FIELD OF THE INVENTION

The present invention relates to a method of extruding products based on N-acylchitosan, and articles made thereof, including shaped medical devices having improved mechanical strength and shape-memory stability.

BACKGROUND OF THE INVENTION

Chitin and chitosan represent a family of biopolymers, made up of N-acetyl-D-glucosamine and D-glucosamine subunits. Chitin can be found widely in the exoskeletons of arthropods, shells of crustaceans, and the cuticles of insects. Chitosan, although occurring in some fungi, is produced industrially by alkaline hydrolysis of chitin. Their different solubilities in dilute acids are commonly used to distinguish between both polysaccharides. Chitosan, the soluble form, can have a degree of acetylation between 0% and about 60%, the upper limit depending on parameters such as processing conditions, molar mass, and solvent characteristics.

Both chitin and chitosan are promising polymers for a variety of applications, including water treatment (metal removal, flocculant/coagulant, filtration), pulp and paper (surface treatment, photographic paper, copy paper), cosmetics (make-up powder, nail polish, moisturizers, fixtures, bath lotion, face, hand and body creams, toothpaste, foam enhancing), biotechnology (enzyme immobilization, protein separation, chromatography, cell recovery, cell immobilization, glucose electrode), agriculture (seed coating, leaf coating, hydroponic/fertilizer, controlled agrochemical release), food (removal of dyes, solids and acids, preservatives, color stabilization, animal feed additive), and membranes (reverse osmosis, permeability control, solvent separation). Of particular interest are biomedical applications of chitin and chitosan because of their biocompatibility, biodegradability and structural similarity to the glycosaminoglycans. Applications and potential applications include dressings for wound-healing, tissue engineering applications, artificial kidney membranes, drug delivery systems, absorbable sutures, hemostats, antimicrobial applications, as well as applications in dentistry, orthopedics, ophthalmology, and plastic surgery. For comprehensive reviews of potential applications of chitin and chitosan see, for example, [Applications of chitin and chitosan, 1997. Shigemasa and Minami, Biotech Genetic Eng Rev 1996; 13:383-420. Ravi Kumar, React Funct Polym 2000; 46:1-27. Singh and Ray, J Macromol Sci 2000; C40:69-83].

However, despite a great variety of potential applications of chitin and chitosan, only a few products are actually in commercial use. One of the major limiting factors for a still broader utilization is the limited capability for extruding these polysaccharides in an efficient manner to products having the desired properties. As an example, chitin and chitosan fibers are usually made by wet-spinning processes, which produce fibers by first dissolving the polymer in a solvent and then extruding the polymer solution into a nonsolvent. However, chitin is insoluble in common solvents, which prevents facile processing. For example, surgical suture made of chitin fiber has been described in U.S. Pat. No. 3,988,411 to Capozza and U.S. Pat. No. 4,932,404 to Kifune et al. which is fabricated by wet-spinning processes using toxic, corrosive, and expensive halogenated solvents. N,N-dimethylacetamide containing lithium chloride has been shown to be an effective alternative solvent system for chitin, overcoming some of the issues associated with halogenated solvents. For example, as described in U.S. Pat. No. 4,059,457 to Austin, chitin fibers can be fabricated using this solvent system by extrusion into an acetone coagulation bath. However, a general problem remains with the removal of the lithium chloride from the fiber. The lithium acts as a Lewis acid solvating the chitin amide group, and it is unclear if this can be completely reversed through washing, once the fiber has been formed. These issues as well as general aspects of chitin fiber processing and solvent systems have been reviewed thoroughly [Rathke and Hudson, J Mater Sci 1994; C34:375437. Agboh and Qin, Polym Adv Tech 1997; 8:355-365. Ravi Kumar, React Funct Polym 2000; 46:1-27].

Chitosan is more readily soluble, and fibers can be prepared by extrusion of diluted acidic solutions of chitosan into an alkaline coagulation bath, such as described in U.S. Pat. No. 2,040,880 to Rigby. However, chitosan fibers fabricated in this manner have low mechanical strength in physiological environment, requiring a subsequent covalent cross-linking procedure [Knaul et al., J Polym Sci 1999; B37:1079-1094]. Methods to improve the mechanical strength of chitosan articles, such as fibers and tubes, have also been suggested in U.S. Pat. No. 6,368,356 to Zhong et al., by using a combined ionic and covalent cross-linking process. However, covalent cross-linking regularly involves toxic chemical substances and by-products which may be difficult to remove from the product. Cross-linking also alters the natural chemical structure of the biopolymer, thereby affecting natural biodegradation processes and products. Additionally, the mechanical strength of ionically and/or covalently cross-linked chitosan is still poor under physiological conditions, and articles having a memorized shape such as those described in '356 quickly loose their shape under physiological conditions.

In "Study of a chitin-based gel as injectable material in periodontal surgery", Biomaterials 2002; 23:1295-1302, Gerentes et al. disclose a treatment of periodontal disease by means of injecting a mixture containing chitosan and acetic anhydride before gelation. In "Chitin-based tubes for tissue engineering in the nervous system", Biomaterials 2005; 26:4624-4632, Freier et al. disclose a method of manufacturing tubes by means of injecting a mixture containing chitosan and acetic anhydride into a mold before gelation.

By considering the aforementioned limitations in the prior art it would be advantageous to manufacture chitin/chitosan-based fibers, tubes and other articles by a simple, inexpensive and efficient process, without the use of toxic solvents and cross-linking agents, and without the release of toxic by-products. It would further be advantageous to manufacture chitin/chitosan-based fibers, tubes and other articles by an extrusion process, leading to sufficient mechanical strength of the extruded products under physiological conditions. It would further be advantageous to manufacture chitin/chitosan-based shaped articles which have an improved mechanical stability under physiological conditions, including a mechanically stable shape-memory which allows the article to be reversibly shaped in different conformations. It would further be advantageous to manufacture chitin/chitosan-based shaped articles which allow for controlled degradation and/or dissolution to non-toxic products under physiological conditions. These and other needs are met in the present invention.

SUMMARY OF THE INVENTION

In the description of the present invention, the term "chitin" is used for a naturally derived polymer made up of either N-acetyl-D-glucosamine subunits or N-acetyl-D-glucosamine and D-glucosamine subunits that is non-soluble in dilute acids. The term "chitosan" is used for a polymer made up of either D-glucosamine subunits or N-acetyl-D-glucosamine and D-glucosamine subunits that is either naturally derived or synthetically prepared by hydrolysis of chitin and that is soluble in dilute acids. The term "N-acylchitosan" represents a polymer that is synthetically prepared by N-acylation of chitosan or that is synthetically prepared by N-acylation or hydrolysis of an N-acylchitosan prepared by N-acylation of chitosan. The term "N-acylchitosan hydrogel" is used for an N-acylchitosan network that is swollen in an aqueous environment. The term "acylation" is used for the N-acylation of the amine group of chitin, chitosan or N-acylchitosan. Accordingly, "acetylation" describes the N-acetylation of chitin, chitosan or N-acylchitosan. The term "deacylation" is used for the N-deacylation of the amide group of chitin, chitosan or N-acylchitosan. Accordingly, "deacetylation" describes the N-deacetylation of chitin, chitosan or N-acylchitosan.

It is an object of the present invention to provide a better process of manufacturing an article containing N-acylchitosan.

It is a further object of the present invention to provide an extrusion process to manufacture chitin/chitosan-based products which overcomes limitations in the prior art, such as the use of toxic solvents and cross-linking agents, as well as insufficient mechanical strength of extruded products under physiological conditions.

In accordance with the present invention, there are provided processes of manufacturing an article containing N-acylchitosan: a process of manufacturing an article containing N-acylchitosan, the process comprising the steps of providing a mixture containing chitosan and/or N-acylchitosan, and extruding the mixture to form an N-acylchitosan hydrogel; a process of manufacturing an article containing N-acylchitosan, the process comprising the steps of providing a chitosan and/or N-acylchitosan hydrogel, and extruding the hydrogel; and a process of manufacturing an article containing N-acylchitosan, the process comprising the steps of providing an N-acylchitosan hydrogel fixed in a desired shape, and at least partially drying the hydrogel, thereby forming an article with a memorized shape.

In accordance with the present invention, there is provided an extrusion process which may comprise of: a) providing a mixture containing chitosan and/or N-acylchitosan, and b) extruding the mixture, thereby essentially instantly forming an N-acylchitosan hydrogel.

In accordance with the present invention, there is provided an extrusion process which may comprise the extrusion of the mixture into a hydrogelation medium capable of promoting the formation of an N-acylchitosan hydrogel.

In accordance with the present invention, there is provided an extrusion process which may comprise the extrusion of a mixture containing chitosan into a mixture containing an acylation agent, thereby essentially instantly forming an N-acylchitosan hydrogel upon extrusion.

In accordance with the present invention, there is provided an extrusion process which may comprise the addition of an acylation agent to the chitosan mixture prior to extrusion in order to increase the degree of acylation of chitosan thereby facilitating the gel formation upon extrusion.

In accordance with the present invention, there is provided an extrusion process which may involve a mixture, solution, or gel extruded.

In accordance with the present invention there is provided an extrusion process which may comprise the steps of providing a chitosan and/or N-acylchitosan hydrogel having shear-thinning properties and extruding the hydrogel.

In accordance with the present invention there is provided an extrusion process which may comprise the steps of providing a chitosan and/or N-acylchitosan hydrogel and extruding the hydrogel, and wherein prior to extrusion the components of the chitosan and/or N-acylchitosan hydrogel may have essentially completely reacted.

In accordance with the present invention, there is provided an extrusion process which may involve hydrolysis of the extruded product, thereby forming a product having improved mechanical strength.

In accordance with the present invention, there is provided an extrusion process which may involve at least partial drying of the extruded product, thereby forming a product having improved mechanical strength.

In accordance with the present invention, there is provided an extrusion process which may involve coating of the extruded product, thereby forming a product having improved mechanical strength.

In accordance with the present invention, there is provided an extrusion process which may involve one or more of the aforementioned modifications of the extruded product, thereby controlling its mechanical, biocompatibility and biodegradation properties.

In accordance with the present invention, there is provided an extrusion process which may be suitable for the fabrication of N-acylchitosan gels, fibers, tubes, films, and other articles.

It is further an object of the present invention to provide a shaped article based on N-acylchitosan which overcomes limitations in the prior art, such as the use of toxic substances and release of toxic by-products during processing, poor stability of mechanical properties and shape memory, and limited control of degradation and dissolution when used as a temporary implant material.

It is another object of the present invention to provide a better method, product and system for the medical treatment of a patient.

In accordance with the present invention, there is provided a shape article. Further in accordance with the present invention, there are provided systems for the medical treatment of a patient: a system for the medical treatment of a patient, characterized in that the system comprises an injectable N-acylchitosan hydrogel, and means for injecting the N-acylchitosan hydrogel into the patient; and a system for delivering a therapeutic agent into a patient, characterized in that the system comprises an injectable N-acylchitosan hydrogel comprising the therapeutic agent, and means for injecting the N-acylchitosan hydrogel into the patient. Further in accordance with the present invention, there are provided methods for the medical treatment of a patient; a method of treating a patient comprising the steps of providing an N-acylchitosan hydrogel, and injecting the N-acylchitosan hydrogel into the patient; and a method of delivering a therapeutic agent comprising the steps of providing an N-acylchitosan hydrogel comprising the therapeutic agent, and injecting the N-acylchitosan hydrogel into a patient. Further in accordance with the present invention, there are provided uses of an injectable N-acylchitosan hydrogel; use of an injectable N-acylchitosan hydrogel for the medical treatment of a patient; and use of an injectable N-acylchitosan hydrogel comprising a therapeutic agent for delivering the therapeutic agent into a patient. Finally in accordance with the present invention, there is provided an injectable N-acylchitosan hydrogel comprising a therapeutic agent.

In accordance with the present invention, there is provided a shaped article, which is made by providing an N-acylchitosan gel, which is fixed in the desired shape, and which is dried under controlled conditions to memorize the shape.

In accordance with the present invention, there is provided a shaped article made of N-acylchitosan, which may have a shape memory, allowing the article to be reversibly shaped in different conformations for ease of use such as implantation into a body.

In accordance with the present invention, there is provided a shaped article which may be made by at least partial drying of N-acylchitosan gel having one or more of the following structures: rod, fiber, tube, film, sphere or other geometric structures which may be hollow or not.

In accordance with the present invention, there is provided a shaped article which may be made by at least partial drying of N-acylchitosan gel, which is conformable to the shape of a medical device or part of a medical device, including the shape of an anchor, hook, coil, mesh, textile, foam, scaffold, stent, catheter, tube, sphere, particle, plug, plate, screw, pin, tack, clip, ring, drug-release depot, cell-encapsulation device.

In accordance with the present invention, there is provided a shaped article which may be a coating, made by at least partial drying of N-acylchitosan gel, of a medical device or part of a medical device, including an anchor, hook, fiber, coil, mesh, textile, foam, sponge, scaffold, stent, catheter, tube, sphere, particle, plug, plate, screw, pin, tack, clip, ring, drug-release depot, cell-encapsulation device.

BRIEF DESCRIPTION OF THE DRAWINGS

FIG. 9A is a side-view of a part of the device, and FIG. 9B is a cross-section of the tube.

FIG. 11 illustrates a coated solid, and FIG. 12 a coated hollow, part of a device.

DETAILED DESCRIPTION OF THE INVENTION

Figure 1:
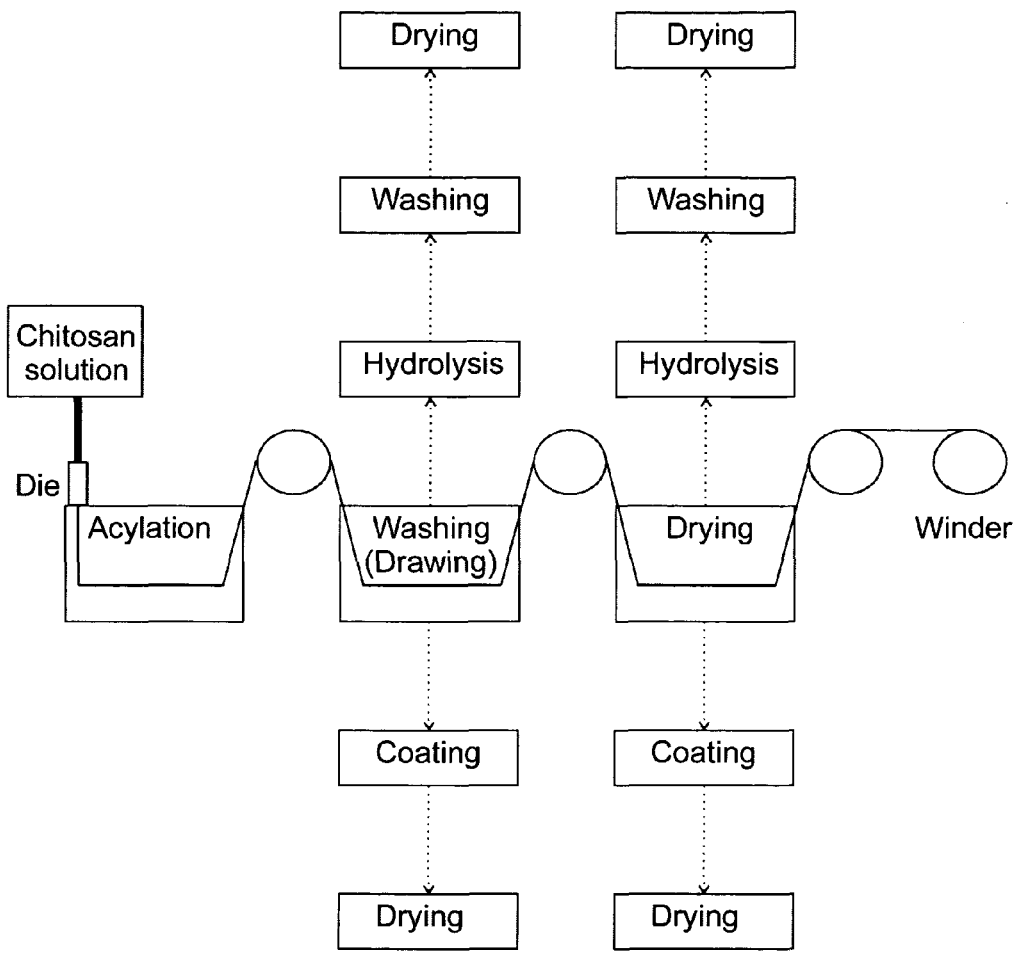
FIG. 1 illustrates one preferred design of the extrusion process including optional steps of hydrolysis, drying, and coating.

In one preferred embodiment, the invention relates to a method of extruding articles based on N-acylchitosan. More particularly, the invention relates to an extrusion process for the fabrication of gels, fibers, tubes, films, and other articles. Extruded articles according to the present invention may include non-medical and medical products. Additionally, extruded articles according to the present invention may be used to fabricate non-medical and medical products. Non-medical products which may consist in total or in part of an extruded article according to the present invention may include separation membranes (gas separation, dialysis, reverse osmosis, ultrafiltration), affinity filtration membranes (chromatography), encapsulation membranes (cells, enzymes), coatings in agriculture (seeds, agrochemicals), water and air treatment products (removal of heavy metals and dyes, air-cleaners), textiles, cosmetics, sanitary products (diapers, panty liners, tampons), food additives, and others. Medical products which may consist in total or in part of an extruded product according to the present invention may include sutures, suture fasteners, slings, coils, rivets, tacks, staples, clips, hooks, buttons, snaps, orthopedic pins/clamps/screws/dowels/plates, bone substitutes, spinal cages/plates/rods/screws/discs, finger joints, intramedullary nails, hip prosthesis, meniscus repair devices, knee replacement devices, cartilage repair devices, ligament and tendon grafts, tendon repair devices, surgical mesh, surgical repair patches, hernia patches, pericardial patches, cardiovascular patches, adhesion barriers, abdominal wall prosthesis, catheters, shunts, stents (coronary, gastrointestinal, esophageal, biliary, ureteral, urethral, stents for aortic aneurysms), vascular grafts and substitutes, coronary artery bypass grafts, guided tissue repair/regeneration devices, scaffolds for tissue engineering, nerve guides, septal defect repair devices, heart valves, vein valves, artificial fallopian tubes, drainage tubes and implants, intrauterine devices, intraocular implants, keratoprosthesis, dental implants, orbital floor substitutes, skin substitutes, dural substitutes, intestinal substitutes, fascial substitutes, wound dressings, burn dressings, medicated dressings, gauze/fabric/sheet/felt/sponge for hemostasis, gauze bandages, bandages for skin surfaces, adhesive bandages, bulking and filling agents, drug delivery matrices, injectable gels and systems, coatings applied to pacemaker leads, implantable sensor wire leads, wires for interventional cardiology, or biosensors, and others.

The extruded articles according to the present invention are made by N-acylation of chitosan forming N-acylchitosan gels. The selective N-acylation reaction of chitosan forming N-acylchitosan gels is well-known in the art and usually includes the treatment of chitosan, which is dissolved in diluted acidic solution and mixed with a cosolvent, with an acyl anhydride. After mixing of the components, gel formation occurs within a few seconds to hours, depending on the reaction conditions and used reactants. However, this method of gel formation known in the prior art is impracticable for application to an extrusion process which requires instant and continuous formation of self-supporting structures under steady-state conditions. Mixture of all components of the acylation reaction prior to the extrusion would be associated with an inhomogeneous process characterized by changing properties of the extruded mixture including increase in the solution viscosity, beginning of gelation including formation of microgels in the solution, and finally complete gelation, which is impracticable to control in a commercial extrusion setup.

According to one preferred embodiment of the present invention, there is provided an extrusion process comprising dissolution of chitosan in a diluted acid, addition of a cosolvent to the chitosan solution, and extrusion of the mixture into a solution containing an appropriate amount of an acylation agent, thereby essentially instantly forming an N-acylchitosan hydrogel upon extrusion. This inventive method allows for an extrusion under steady-state conditions as required for processes such as wet-spinning of fibers and hollow fibers (tubes).

In a typical setup, the extrusion line is comprised of a reservoir containing the chitosan solution which will be filtered (by passing through a filter either before adding to the reservoir or while leaving the reservoir, as it is known in the art) and degassed (e.g. by evacuation or sonication, as it is known in the art) and which will be forced, by means of a pump, through a die (e.g. a single- or multi-hole fiber spinneret, or a coaxial tube spinneret) into the acylation bath for gelation (FIG. 1). Take-up rollers at the end of the acylation bath will be maintained at a velocity which prevents kinking of the N-acylchitosan gel article formed. Following gelation in the acylation bath, the extruded article will be washed by passing through a bath containing water which is maintained at room temperature. The extruded article may simultaneously (to the washing step) be subjected to drawing, by rotating the take-up roller at the end of the water bath at a higher speed than the advancing roller at the beginning of the water bath. Drawing may be performed at room temperature or at elevated temperature. The extruded article may then be dried by passing through a drying bath containing one or more organic drying agents known in the art, such as acetone, ethanol and isopropanol, and/or air-dried by convection at room temperature or elevated temperature, before being wound up on a winder. Alternatively, as it will be outlined in detail further below, the extruded article may be subjected to hydrolysis and/or coating procedures before or after drying. Furthermore, as it will be outlined in detail further below, drying may be performed in such a way that a specific shape-memorized design will be implemented in the extruded article.

The most preferable acylation agent for use according to the present invention is acetic anhydride; however, other acylation agents, including, for example, propionic, butyric, hexanoic, octanoic, decanoic, maleic, and methacrylic anhydride may be used for gel formation. Suitable solvents for chitosan include dilute inorganic and organic acids, such as formic, acetic, propionic, lactic, and citric acid; most preferable to manufacture gels for use according to the present invention is aqueous acetic acid. Suitable cosolvents to be added to the chitosan solution as well as solvents to be added to the acylation bath (i.e., to dissolve/dilute the acylation agent) include water as well as organic liquids, such as methanol, ethanol, propanol, butanol, trifluoroethanol, ethylene glycol, diethylene glycol, polyethylene glycol, glycerol, formamide, N,N-dimethyl formamide, N-methylpyrrolidone, dimethyl sulfoxide, dioxane, and tetrahydrofurane. Most preferable to manufacture gels for use according to the present invention are ethanol and methanol. The well-known fact that N-acylchitosan hydrogels are practically insoluble in most common solvents allows for gel formation in a broad variety of acylation baths made of different acylation agent/solvent mixtures, and the use of mixtures of different acylation agents as well as solvent mixtures.

Preferred products extruded according to the present invention are those based on N-acetylchitosan. Preferably, the extrusion involves dissolution of 2-10% chitosan in 0.5-15% aqueous acetic acid, addition of a 1-2.5 fold volume of ethanol, and extrusion of the resulting homogeneous mixture into an acylation bath containing a solution of 10-90% acetic anhydride in ethanol. More preferably, chitosan is dissolved in a concentration of 3-5% in 2-5% aqueous acetic acid, mixed with a 1-2 fold volume of ethanol, and extruded into an acylation bath containing 25-50% of acetic anhydride in ethanol (Example 1).

Preferably, the chitosan used as starting material for extrusion processes according to the present invention has a degree of acetylation of less than 25% and a viscosity between approximately 200-2000 mPas (analyzed as 1% solution in 1% acetic acid on a Brookfield viscometer at 25.degree. C.). More preferably, the chitosan has a degree of acetylation of less than 15% and a viscosity between approximately 200-1000 mPas.

Methanol may be beneficial over ethanol under specific conditions, particularly if higher concentrations of chitosan are used. In this case, chitosan is preferably dissolved in a concentration of 5-7% in 2-5% aqueous acetic acid, mixed with a 1-2 fold volume of methanol, and extruded into an acylation bath containing 25-50% of acetic anhydride in either ethanol or methanol (see Example 1). Extrusion may also be performed into a pure acylation agent without addition of any solvent to the acylation bath. The extrusion process may preferably be performed at room temperature; however, higher temperatures, up to approximately 60.degree. C., of the extruded mixture and/or acylation bath may be used to accelerate the gelation process.

Figure 2:
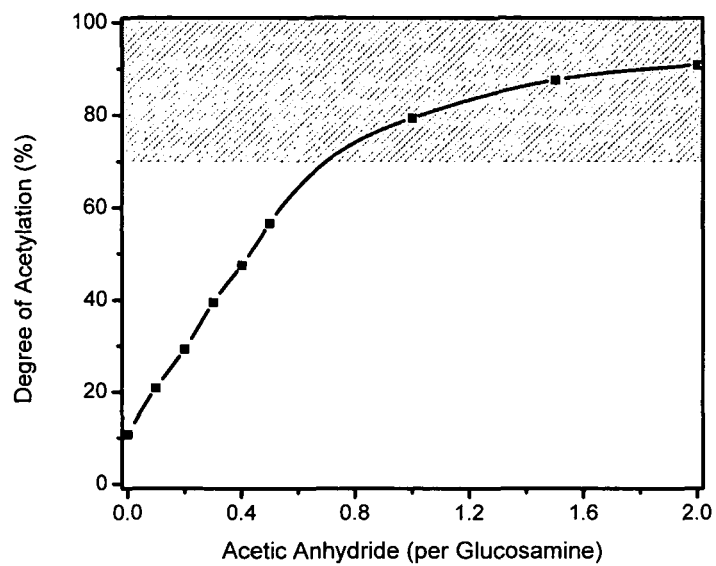
FIG. 2 is an illustrative example of a selective N-acylation reaction forming N-acetylchitosan hydrogels. Gelation occurs by addition of more than approximately 0.7-fold acetic anhydride to the chitosan solution (per glucosamine unit of chitosan, degree of acetylation at start 11%), which is equivalent to a degree of acetylation greater than approximately 70% (shadowed area).

Another method to accelerate the gelation of the chitosan mixture upon extrusion into the acylation bath is to use chitosan having a high degree of acylation of up to approximately 60%, or to incorporate a pre-acylation step of chitosan to increase its degree of acylation prior to extrusion, by addition of an acylation agent to the chitosan solution/cosolvent mixture (see Example 1). The acylation agent used for pre-acylation may be equal or different to that used for the acylation bath. It is a preferred embodiment of the present invention that, in order to allow for a homogeneous extrusion process, the components of the pre-acylation reaction have essentially completely reacted prior to extrusion. Pre-acylation is preferably performed by using an appropriate amount of acylation agent, so that the formed N-acylchitosan remains completely dissolved without gel formation prior to extrusion. For example, N-acetylchitosan gels are usually formed by addition of more than 0.7 fold acetic anhydride to a solution of chitosan, having a degree of acetylation of 11% at start, in 2% aqueous acetic acid mixed with an equal volume of ethanol, which is equivalent to a degree of acetylation of the product greater than 70% (FIG. 2). According to this example, the amount of acetic anhydride for pre-acetylation should be less than 0.7 fold so that the formed N-acetylchitosan is less than 70% acetylated, thereby remaining soluble prior to extrusion. More generally, pre-acetylation is preferably performed by addition of a 0.3-0.7 fold molar amount of acetic anhydride to the chitosan solution (per glucosamine unit of chitosan). The amount of acyl anhydride other than acetic anhydride that may be added to a chitosan solution for the purpose of pre-acylation without gel formation prior to extrusion depends on the chemical nature. Generally, the more hydrophobic the acyl anhydride the less the amount that may be added. The amount of acyl anhydride that may be added to a chitosan solution for the purpose of pre-acylation without gel formation prior to extrusion also depends on the amount of cosolvent added to the chitosan solution. Generally, the higher the cosolvent content the less the amount of acyl anhydride that may be added.

Alternatively, pre-acylation may result in a gel which is extrudable utilizing the shear-thinning properties of N-acylchitosan gels. In this latter case, extrusion into an acylation bath may be applied if products of high mechanical strength are desired. However, in specific applications, extrudates having low to moderate mechanical strength may be sufficient so that extrudable gels may be applied without the step of extrusion into an acylation bath. Such an example may be an injectable system for application in a patient for the purpose of filling or bulging, or to deliver therapeutic agents, taking advantage of the shear-thinning properties of N-acylchitosan gels, which enable these gels to be extrudable directly through a needle via a syringe-extrusion in a steady-state manner. N-acylchitosan gels having appropriate shear-thinning properties making them suitable for injection are those having moderate degrees of acylation, usually below 90% and preferably below 80%, in order to decrease injection forces. Among N-acylchitosan gels, N-acetylchitosan gels are preferably used as injectable gels according to the present invention. For example, an N-acetylchitosan gel which is formed by addition of a 0.7 fold molar amount of acetic anhydride to a 3% chitosan solution in 2% aqueous acetic acid mixed with an equal volume of ethanol can easily be applied using a 30 gauge needle. The amount of acetic anhydride required for gel formation depends on the amount of cosolvent added, as outlined above. Thus for example, addition of a 0.5 fold amount of acetic anhydride to a solution of 3% chitosan in 2% aqueous acetic acid mixed with a twofold amount of ethanol likewise results in an N-acetylchitosan gel extrudable through a 30 gauge needle (Example 2).

In a preferred embodiment of the present invention, prior to extrusion the components of the chitosan and/or N-acylchitosan hydrogel have essentially completely reacted. In this context, "completely reacted" refers to the acylation of the 2-amino-group of the chitosan and/or N-acylchitosan. It can be an advantage of this embodiment of the invention that the hydrogel is of a well-defined consistency regardless of the exact time of extrusion.

Applications of injectable gels made of N-acylchitosan may be found, for example, in tissue engineering, in order to repair soft tissue, cartilage or bone defects. Another potential application is to fill cerebral aneurysms, taking advantage of the hemostatic capability of chitosan. Additionally, injectable N-acylchitosan gels may be used to fill irregularly-shaped tissue defects or to improve the facial texture by treating wrinkles, creases, furrows, sunken cheeks, or scars. An advantage of injectable gels such as N-acylchitosan gels is that they may be used to repair tissue defects in a minimally-invasive manner. These gels may also be used to deliver therapeutic agents, such as drugs to treat cancer, infections, inflammations, pain, and diseases/disorders of the central nervous system.

As described, extrusion may be performed using solutions or gels. More generally, different types of mixtures may be extruded. This also includes well-homogenized mixtures comprising different phases or suspensions. The extrudate may contain additives including, for example, acids, bases, plasticizers, fillers, dyes, porogens, contrast agents, microparticles, nanoparticles, bioactive agents and drugs. Such additives may be added to the reaction mixture prior to gel formation, and/or may be added to the acylation bath in which the gel is formed upon extrusion.

In accordance with the present invention, the extrusion process may involve a subsequent hydrolysis step of the extruded product, thereby forming a product having improved mechanical strength. Generally, hydrolysis may be performed before or after drying of the extruded product. Hydrolysis (deacylation) may lead to a product having a very low degree of acylation which increases the mechanical strength. Hydrolysis may be performed by storage of the extruded N-acylchitosan gel in a concentrate alkaline solution at elevated temperature, such as for example in 40% aqueous sodium hydroxide solution at 110.degree. C. for 2 hours (Example 3, FIG. 3). More generally, hydrolysis may be performed by storage of N-acylchitosan in a 10-50% aqueous alkaline solution at 50-120.degree. C. for up to 4 hours. Preferably, hydrolysis may be performed using a 20-40% aqueous alkaline solution at 70-110.degree. C. for 0.5-2 hours. Hydrolysis may also be performed in several cycles in order to further decrease the degree of acylation and improve the mechanical strength under physiological conditions. Preferably, 1-3 cycles of hydrolysis may be used according to the present invention (Example 3, FIG. 4). Additionally, hydrolysis may be particularly suitable for extruded N-acylchitosan gels formed by using acyl anhydrides different from acetic anhydride, in order to completely remove the acyl group and re-establishing the natural chemical structure of the biopolymer.

It is in the scope of the present invention to include also those N-acylchitosan gels which are essentially free of N-acyl groups due to several cycles of hydrolysis. It will be understood by those skilled in the art that 100% deacylation of N-acylchitosan is only of theoretical interest and that in practice even in materials which are essentially free of N- acyl groups some N-acyl groups still remain in the chemical structure so that these materials are also referred to as N-acylchitosan with respect to the present invention.

Figure 5:
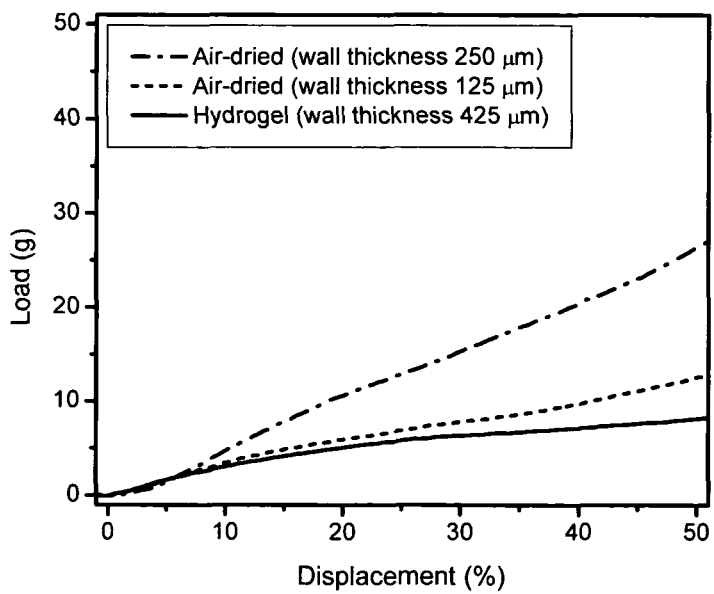
FIG. 5 illustrates typical load-displacement curves of N-acetylchitosan gel and air-dried tubes (in phosphate buffered solution, 37.degree. C.).

In accordance with the present invention, the extrusion process may also involve a subsequent drying step of the extruded product, thereby forming a product having improved mechanical strength (Example 4, FIG. 5). N-acylchitosan hydrogels are highly porous, comprising a honeycomb-like morphology which collapses irreversibly during drying, leading to a denser packing of the polymer bulk and higher mechanical strength under physiological conditions. It should be understood that "drying" with respect to the present invention includes processes leading to the removal of liquid components including water and other solvents from the hydrogel. Drying may preferably be performed by storage of the extruded N-acylchitosan gel product on air and at room temperature. Similarly, any gas which may flow or not, may be used for the drying process. Other methods include the application of higher temperatures and/or vacuum during storage. The temperatures and methods chosen for drying should be appropriate to prevent decomposition, cross-linking and other changes in the chemical structure of the N-acylchitosan gel. Drying may be performed completely, which may take several minutes to hours depending on the geometry and thickness of the product, or partially, for a defined period of time, in order to define the properties of the final product. After fabrication of dried articles, they may simply be stored in a dry atmosphere, or they may be stored in an aqueous environment. Dried articles for medical applications can easily be sterilized, preferably with ethylene oxide, hydrogen peroxide plasma, or gamma irradiation. Dried articles are usually relatively stiff, but become flexible when re-immersed in aqueous solution which facilitates their handling, including implantation into a body, and which allows for comfort to the patient during and after implantation.

In accordance with the present invention, the extruded product may also be modified by coating with a layer of a polymer or other compound, which may be applied from solution by one of the techniques well-known in the art, such as dipping or spraying. Generally, coating may be applied before or after drying of the extruded product. Additionally, coating may be applied to the hydrolyzed product, before or after its drying. For example, a layer of a biodegradable polymer may be formed on the surface of a product in order to control its properties, including mechanical strength, biocompatibility, biodegradation, diffusibility, and adsorption properties. Suitable biodegradable polymers include, for example, those from the group of synthetic polyesters, such as homopolymers and copolymers based on glycolide, L-lactide, D,L-lactide, p-dioxanone, E-caprolactone; natural polyesters, such as those from the group of the polyhydroxyalkanoates, such as homopolymers and copolymers based on 3-hydroxybutyrate, 4-hydroxybutyrate, 3-hydroxyvalerate, 3-hydroxyhexanoate, 3-hydroxyoctanoate; polyorthoesters; polycarbonates; polyanhydrides; polyurethanes; polyphosphazenes; polyphosphoesters; polysaccharides; polypeptides; as well as derivatives, copolymers, and blends based on the abovementioned and any other group of bioresorbable polymers. Other suitable polymers include those which may be dissolved under physiological conditions, such as homopolymers or copolymers based on vinyl alcohol, vinyl acetate, N-vinyl pyrrolidone, ethylene glycol, propylene glycol, polysaccharides, polypeptides, as well as derivatives, copolymers, and blends based on the aforementioned and any other group of biodissolvable polymers or combinations of biodegradable and biodissolvable polymers. Furthermore, it is possible to coat the article with a non-degradable or non-dissolvable polymer for specific applications of the extruded article, which require to prevent its degradation.

The polymer layer may further contain additives, including acids, bases, plasticizers, fillers, dyes, porogens, contrast agents, microparticles, nanoparticles, bioactive agents and drugs. Such additives may be added to the polymer solution prior to the coating process. In another example, a layer of a contrast agent may be formed on the surface of the extruded article after its fabrication. For example, a layer of barium sulfate may be formed by dipping the article into an aqueous solution of a barium salt, followed by dipping into an aqueous solution containing sulfate ions, thereby forming a layer of barium sulfate on the surface of the article. In yet another example, a layer of a bioactive agent or drug may be formed on the surface of the extruded article. For example, a layer of a bioactive agent or drug may be applied to the surface using an aqueous solution or organic solvent, followed by drying.

In accordance with the present invention, there is provided an extrusion process for the fabrication of N-acylchitosan gels, fibers, tubes, films, and other articles, which may be hollow or not. Tubes may have a single lumen or multiple lumens, and they may be single- or multilayered. Tube extrusion may involve a gaseous, liquid or solid core component for stabilizing the internal tube dimensions, as it is known in the art. The initial shape of the extruded product is defined by the design of the die used in the extrusion process. Die designs are well-known in the art and include sheet dies, profile dies, tubing dies, and coating dies. The variation of die designs allows for the extrusion of N-acylchitosan gel articles in different cross-sectional shapes, such as the fabrication of cylindrical, triangular, quadrangular, and in general, polygonal tubes. Moreover, as it has been outlined above and also shown on the example of N-acetylchitosan gel tubes (FIG. 5), drying of the extruded product results in improved mechanical strength. The higher compression strength of tubes after drying (see FIG. 5) further implies a higher stability of the tubular (cross-sectional) shape. Such for example, a dried tube which is fabricated according to the present invention can be cut open longitudinally without losing its tubular (cross-sectional) shape stability which would be, for example, of advantage in applications as a wrap around structures to be stabilized, such as damaged or diseased nerve.

However, extrusion through a die does not provide any means to form specific designs (shapes) in the longitudinal direction of the extruded N-acylchitosan gel article. It is therefore another preferred embodiment of the present invention to provide shaped articles based on N-acylchitosan having improved mechanical strength and shape-memory stability not only in the cross-sectional but also longitudinal direction. Furthermore, it is in the scope of the present invention to provide a process for implementing shape-memorized designs into N-acylchitosan articles without affecting biocompatibility and biodegradation properties which is of particular importance for medical devices. Shaped medical devices according to this embodiment of the present invention may include those based on fibers, including coils, dressings, meshes, gauzes and similar structures. Furthermore, shaped medical devices according to this embodiment of the present invention may include those based on tubular structures, including biliary, urinary and vascular stents, catheters, cannulas and similar devices. Additionally, they may include screws, plates, rods, anchors, plugs, fillers, capsules and any other shaped medical device. Preferred devices include sutures, suture fasteners, slings, coils, rivets, tacks, staples, clips, hooks, buttons, snaps, orthopedic pins/clamps/screws/dowels/plates, bone substitutes, spinal cages/plates/rods/screws/discs, finger joints, intramedullary nails, hip prosthesis, meniscus repair devices, knee replacement devices, cartilage repair devices, ligament and tendon grafts, tendon repair devices, surgical mesh, surgical repair patches, hernia patches, pericardial patches, cardiovascular patches, adhesion barriers, abdominal wall prosthesis, catheters, shunts, stents (coronary, gastrointestinal, esophageal, biliary, ureteral, urethral, stents for aortic aneurysms), vascular grafts and substitutes, coronary artery bypass grafts, guided tissue repair/regeneration devices, scaffolds for tissue engineering, nerve guides, septal defect repair devices, heart valves, vein valves, artificial fallopian tubes, drainage tubes and implants, intrauterine devices, intraocular implants, keratoprosthesis, dental implants, orbital floor substitutes, skin substitutes, dural substitutes, intestinal substitutes, fascial substitutes, wound dressings, burn dressings, medicated dressings, gauze/fabric/sheet/felt/sponge for hemostasis, gauze bandages, bandages for skin surfaces, adhesive bandages, bulking and filling agents, drug delivery matrices, injectable gels and systems, coatings applied to pacemaker leads, implantable sensor wire leads, wires for interventional cardiology, or biosensors, and others.

The shaped medical devices according to this embodiment of the present invention are particularly applicable for use in urogenital, cardiovascular, gastrointestinal, neurological, lymphatic, otorhinolaryngological, opthalmological and dental applications. Additionally, they are particularly interesting for applications in tissue engineering, including those containing steps of cellular seeding.

The shaped articles according to this embodiment of the present invention are made by starting from N-acylchitosan gels. Generally, N-acylchitosan gels used to fabricate shaped articles are made by extrusion in accordance with the present invention. Additionally, N-acylchitosan gels made by other processes which are known in the art may be suitable to fabricate shaped articles. Injection molding is the most preferable method among these other processes.

Preferred gels for the fabrication of shaped articles according to this embodiment of the present invention are those consisting of N-acetylchitosan. Preferably, extrusion involves dissolution of 2-10% chitosan in 0.5-15% aqueous acetic acid, addition of a 1-2.5 fold volume of ethanol, and extrusion of the resulting homogeneous mixture into an acylation bath containing 10-90% acetic anhydride in ethanol, as described above and illustrated in Example 1. More preferably, chitosan is dissolved in a concentration of 3-5% in 2-5% aqueous acetic acid, mixed with a 1-2 fold volume of ethanol, and extruded into an acylation bath containing 25-50% of acetic anhydride in ethanol. Methanol may be beneficial over ethanol under specific conditions, particularly if higher concentrations of chitosan are used. In this case, chitosan is preferably dissolved in a concentration of 5-7% in 2-5% aqueous acetic acid, mixed with a 1-2 fold volume of methanol, and extruded into an acylation bath containing 25-50% of acetic anhydride in either ethanol or methanol. For injection-molding, N-acetylchitosan gels are preferably made by treatment of a solution of 2-5% chitosan in 0.5-10% aqueous acetic acid, the solution being diluted with a 0.5-2 fold volume of ethanol, with a 1-3 fold excess of acetic anhydride. More preferably, a solution of 3-4% chitosan in 2-5% aqueous acetic acid is mixed with a 1-2 fold volume of ethanol, and a 1.5-2.5 fold excess of acetic anhydride is added, as illustrated in Example 5.

In both cases, for extrusion and injection-molding, the chitosan used as starting material has preferably a degree of acetylation of less than 25% and a viscosity between approximately 200-2000 mPas (analyzed as 1% solution in 1% acetic acid on a Brookfield viscometer at 25.degree. C.). More preferably, the chitosan has a degree of acetylation of less than 15% and a viscosity between approximately 200-1000 mPas.

N-acylchitosan gels which are suitable for the fabrication of shaped articles according to this embodiment of the present invention may have the shape of a rod, fiber, tube, film, sphere or other geometric structures which may be hollow or not. The gel may already have a shape similar to that of the desired final product. Fibers, tubes, films, and other articles, which may be hollow or not, may be made by extrusion, as described above and illustrated in Example 1. In an injection-molding process, as illustrated in Example 3, the acylation reaction mixture may simply be injected into a mold of pre-selected size and shape, and will be left for gelation without further application of any forces, in order to allow for homogeneous gel formation. For example, movement of the mold or application of forces to the mold during gel formation may result in inhomogenic gel morphologies which is disadvantageous with respect to the formation of shaped articles according to the present invention. N-acylchitosan gel rods and fibers may be fabricated by injecting the acylation reaction mixture into a cylindrical mold for gel formation (Example 5). Similarly, N-acylchitosan gel tubes may be fabricated by injecting the acylation reaction mixture into a cylindrical mold which contains a centrally fixed core for gel formation (Example 5). Cylindrical molds may contain more than one core to fabricate gel tubes with multiple channels. Corrugated rods and tubes may be fabricated by using a corrugated mold for injection and gel formation. Similarly, other three-dimensional structures may be fabricated by injecting the acylation reaction mixture into appropriate molds for gelation. N-acylchitosan gel films can simply be made by pouring the acylation reaction mixture into a Petri dish or similar container for gel formation, or by injection into a suitable mold. Another technique is to cut a gel tube longitudinally to provide a film for further processing into a shaped article according to the present invention.

Shaped articles according to this embodiment of the present invention having improved mechanical strength and shape-memory stability are fabricated by drying N-acylchitosan gel structures such as those described above under fixation of the desired shape. The collapse of the honeycomb-like morphology of the hydrogel during the dehydration/desolvation process leads to the irreversible preservation of the fixed shape together with improved mechanical stability due to a denser packing of the polymer bulk.

It should be understood that "drying" with respect to the fabrication of shaped articles according to this embodiment of the present invention includes processes leading to the removal of liquid components including water and other solvents from the hydrogel. Drying may preferably be performed by storage of the shape-fixed N-acylchitosan gel on air and at room temperature. Similarly, any gas which may flow or not, may be used for the drying process. Other methods include the application of higher temperatures and/or vacuum during storage. The temperatures and methods chosen for drying should be appropriate to prevent decomposition, cross-linking and other changes in the chemical structure of the N-acylchitosan gel. Drying may be performed completely, which may take several minutes to hours depending on the geometry and thickness of the shape-fixed article, or partially, for a defined period of time, in order to define the properties of the final product. It is important to note that freeze-drying or other processes of drying which prevent the collapse of the honeycomb-like morphology of the gel do not allow for fabrication of articles with suitable mechanical strength and shape-memory properties according to the present invention. After fabrication of dried articles, they may simply be stored in a dry atmosphere, or they may be stored in an aqueous environment. Dried articles can easily be sterilized, preferably with ethylene oxide, hydrogen peroxide plasma, or gamma irradiation. Dried articles are usually relatively stiff, but become flexible when re-immersed in aqueous solution which facilitates their handling, including implantation into a body, and which allows for comfort to the patient during and after implantation.

N-acylchitosan gels suitable for the fabrication of shaped articles according to this embodiment of the present invention may be modified prior to the drying process. The modification may include ionic or covalent binding of a compound, such as a bioactive agent or drug. Other modifications include controlled acylation or hydrolysis reactions, in order to adjust the degree of acylation of the gel, thereby controlling mechanical properties, biodegradation, and biocompatibility. Most preferable is a hydrolysis (deacylation) reaction leading to products having a low degree of acylation which further increases the mechanical strength. Hydrolysis may be performed by storage of the gel in concentrated alkaline solutions at elevated temperatures, such as for example in 40% aqueous sodium hydroxide solution at 110.degree. C. for 2 hours. More generally, hydrolysis may be performed by storage of N-acylchitosan in a 10-50% aqueous alkaline solution at 50-120.degree. C. for up to 4 hours. Preferably, hydrolysis may be performed using a 20-40% aqueous alkaline solution at 70-110.degree. C. for 0.5-2 hours. Hydrolysis may also be performed in several cycles in order to further decrease the degree of acylation and improve the mechanical strength. Preferably, 1-3 cycles of hydrolysis may be used according to the present invention. Additionally, hydrolysis may be particularly suitable for gels formed by using acyl anhydrides different from acetic anhydride, in order to completely remove the acyl group and re-establishing the natural chemical structure of the biopolymer.

The shaped article in accordance with this embodiment of the present invention may contain additives, allowing the article to be designed to the specific requirements. Such additives may include acids, bases, plasticizers, fillers, dyes, porogens, contrast agents, microparticles, nanoparticles, bioactive agents and drugs. Such additives may be added to the reaction mixture prior to gel formation, and/or may be soaked into the gel by storage of the gel in a solution of the additive prior to the drying process. Such additives may also be soaked into the bulk or coated onto the surface of the product after drying.

The shaped article fabricated in accordance with this embodiment of the present invention may further be modified by a method described above for N-acylchitosan gels, including ionic or covalent binding of a compound, such as a bioactive agent or drug, and controlled acylation or hydrolysis reactions, in order to adjust the degree of acylation of the article, thereby controlling mechanical properties, biodegradation, and biocompatibility. Most preferable is a hydrolysis (deacylation) reaction leading to products having a very low degree of acylation which further increases the mechanical strength. Hydrolysis may be performed by storage of the article in concentrated alkaline solutions at elevated temperatures, such as for example in 40% aqueous sodium hydroxide solution at 110.degree. C. for 2 hours. More generally, hydrolysis may be performed by storage of N-acylchitosan in a 10-50% aqueous alkaline solution at 50-120.degree. C. for up to 4 hours. Preferably, hydrolysis may be performed using a 20-40% aqueous alkaline solution at 70-110.degree. C. for 0.5-2 hours. Hydrolysis may also be performed in several cycles in order to further decrease the degree of acylation. Preferably, 1-3 cycles of hydrolysis may be used according to the present invention. Additionally, hydrolysis may be particularly suitable for articles formed by using acyl anhydrides different from acetic anhydride, in order to remove the acyl group and re-establishing the natural chemical structure of the biopolymer.

The shaped article may also be modified by coating with a layer of a polymer or other compound, which may be applied from solution by one of the techniques well-known in the art, such as dipping or spraying. Thus for example, a layer of a biodegradable polymer may be formed on the surface of the shaped article in order to control its properties, including mechanical strength, biocompatibility, and biodegradation. Suitable biodegradable polymers include, for example, those from the group of synthetic polyesters, such as homopolymers and copolymers based on glycolide, L-lactide, D,L-lactide, p-dioxanone, E-caprolactone; natural polyesters, such as those from the group of the polyhydroxyalkanoates, such as homopolymers and copolymers based on 3-hydroxybutyrate, 4-hydroxybutyrate, 3-hydroxyvalerate, 3-hydroxyhexanoate, 3 hydroxyoctanoate; polyorthoesters; polycarbonates; polyanhydrides; polyurethanes; polyphosphazenes; polyphosphoesters; polysaccharides; polypeptides; as well as derivatives, copolymers, and blends based on the abovementioned and any other group of bioresorbable polymers. Other suitable polymers include those which may be dissolved under physiological conditions, such as homopolymers or copolymers based on vinyl alcohol, vinyl acetate, N-vinyl pyrrolidone, ethylene glycol, propylene glycol, polysaccharides, polypeptides, as well as derivatives, copolymers, and blends based on the aforementioned and any other group of biodissolvable polymers or combinations of biodegradable and biodissolvable polymers. Furthermore, it is possible to coat the shaped article with a non-degradable or non-dissolvable polymer for specific applications of the shaped articles, which require to prevent its degradation.

The polymer layer may further contain additives, including acids, bases, plasticizers, fillers, dyes, porogens, contrast agents, microparticles, nanoparticles, bioactive agents and drugs. Such additives may be added to the polymer solution prior to the coating process. In another example, a layer of a contrast agent may be formed on the surface of the shaped article after its fabrication. For example, a layer of barium sulfate may be formed by dipping the shaped article into an aqueous solution of a barium salt, followed by dipping into an aqueous solution containing sulfate ions, thereby forming a layer of barium sulfate on the surface of the shaped article. In yet another example, a layer of a bioactive agent or drug may be formed on the surface of the shaped article. For example, a layer of a bioactive agent or drug may be applied to the surface using an aqueous solution or organic solvent, followed by drying.

In yet another example of modification of the shaped article, an additional layer of N-acylchitosan gel may be applied to the surface of the article and may be dried for shape-fixation. These steps may be repeated several times to fabricate a multilayered article. The N-acylchitosan layers may have different properties such as different degrees of acylation in order to define individual mechanical, biocompatibility, and biodegradation properties of individual layers. The N-acylchitosan layers may be modified by techniques as described above or may contain additives as those described above. Such additives may also be embedded between the layers. In such a design, the additive will be applied to the surface of one layer of the article before adding the next layer of N-acylchitosan gel. The subsequent drying process of this outer layer will lead to the incorporation of the additive between the layers.

In accordance with this embodiment of the present invention, the shaped article is conformable to the shape of a medical device or part of a medical device, including the shape of an anchor, hook, coil, mesh, textile, foam, scaffold, stent, catheter, tube, sphere, particle, plug, plate, screw, pin, tack, clip, ring, drug-release depot, cell-encapsulation device.

Figure 6:
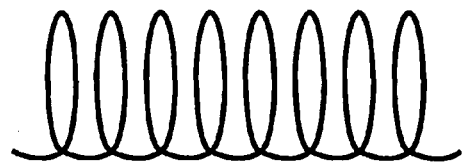
FIG. 6 is an illustration of a shaped medical device made from N-acylchitosan fiber according to the present invention.

For example, a coil may be fabricated by winding an N-acylchitosan gel fiber of defined diameter on a mandrel or screw, fixing the ends of the fiber to maintain the coiled shape, and drying by storage on air, leading to a shape-memorized coiled conformation of the resulting article (Example 6, FIG. 6). More complex three-dimensional structures may be fabricated by drying of N-acylchitosan gel fibers fixed in defined conformations using complex designs of mandrels such as those consisting of a center post with side pins as known in the art. A hollow coil or spiral may be fabricated by winding and fixing an N-acylchitosan gel tube on a mandrel for drying (Example 7, FIG. 7). Tubular articles such as stents and catheters may be fabricated by fixing an N-acylchitosan gel tube in the desired shape during drying. Thus shape-memorized tubular designs may have one or more sections which are shape-memorized in a non-linear conformation with respect to the longitudinal axis of the tube. One particularly interesting shape of a tubular article is that of a ureteral stent having ends in the form of a pigtail ("double-J catheter") (Example 8, FIG. 8). This type of stent may be fabricated by fixing the ends of an N-acylchitosan gel tube in the desired pigtail conformation during the drying process, leading to a shape-memorized pigtail conformation of the resulting article. Another shaped article of particular interest is a Foley catheter, which may be formed by a combination of a two-channel tube and a hollow sphere made of N-acylchitosan (Example 9, FIGS. 9A and 9B). It should be noted that other distorted hollow structures may be used for fabrication of this type of catheter, including ovate, ovoid, or ellipsoid shapes. It is worth noting that urological articles such as stents and catheters would be highly beneficial when made of N-acetylchitosan compared to other materials, due to the inherent antibacterial properties of N-acetylchitosan, thereby limiting and preventing infections which are commonly associated with these implants. N-acetylchitosan may also be highly beneficial as a coating of other materials used in urological applications.

In accordance with this embodiment of the present invention, the shaped article may be formed as a coating, made by starting from an N-acylchitosan gel, of a medical device or part of a medical device, including an anchor, hook, fiber (including fiber bundles), coil, mesh, textile, foam, sponge, scaffold, stent, catheter, tube, sphere, particle, plug, plate, screw, pin, tack, clip, ring, drug-release depot, cell-encapsulation device. This coating may be performed by attaching an N-acylchitosan gel, which may have the shape of a rod, fiber, coil, tube, film, sphere or other geometric structures, to the surface of the device or part of a device to be coated, followed by drying. One or more devices may be coated together in one step.

Figure 10:
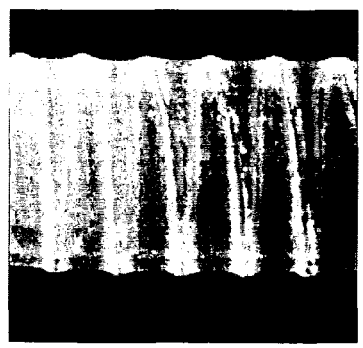
FIG. 10 is an image (side-view) of a coil-shaped medical device which is coated with N-acylchitosan according to the present invention.

Such for example, a coil may be coated by inserting it into an N-acylchitosan gel tube which has an inner diameter slightly larger than the outer diameter of the coil, and drying (Example 10, FIG. 10). Rods, including cylindrical drug pellets (Example 11, FIG. 11), and tubes, including porous tubes (Example 12, FIG. 12) may be coated in a similar manner. As an example, a stent or catheter may be inserted into an N-acylchitosan gel tube of appropriate dimensions, i.e. with an inner diameter slightly larger than the outer diameter of the stent or catheter. The tube will then be dried for shape-fixation and attachment to the underlying stent or catheter. A screw or pin may be inserted similarly into an N-acylchitosan gel tube, followed by its drying leading to attachment to the screw or pin (Example 13, FIG. 13). Fibers and fiber bundles, porous structures, foams, sponges, powders, pellets, or tablets may be coated in a similar manner, by inserting in an N-acylchitosan gel tube or other hollow structure of appropriate dimension, followed by drying. As another example, a fiber or fiber bundle may be inserted into an N-acylchitosan gel tube, and the fiber/gel tube composite will be fixed in a desired shape, such as a coiled shape as described above, for drying and shape-fixation.

Coating may also be performed by dipping a medical device or part of a medical device, including those mentioned above, into the acylation reaction medium, followed by removal and gel layer formation on the surface of the dipped material. Subsequent drying leads to shape-fixation of the N-acylchitosan coating. Modifications as those described above may be applied before and/or after drying, as described above.

EXAMPLES

1. Extrusion of N-acetylchitosan Gel Fibers and Tubes

A 3% solution of chitosan (degree of acetylation 11%) in 2% aqueous acetic acid was diluted with an equal volume of ethanol. A 0.5 fold molar amount of acetic anhydride was added to the solution. The reaction mixture was filtered and degassed, and extruded through a single-hole spinneret (inner diameter 0.25 mm) into a bath containing 50% acetic anhydride in ethanol. The N-acetylchitosan gel fiber formed was washed with distilled water, and air-dried resulting in an N-acetylchitosan fiber having a diameter of approximately 50 .mu.m. N-Acetylchitosan hollow fibers (tubes) were fabricated in a similar manner, by extruding the reaction mixture through a spinneret comprising an annular ring (outer diameter 2.3 mm, width of the annular gap 0.25 mm) through which the chitosan solution passed, and a central bore (diameter 1.5 mm) through which a core liquid consisting of 50% acetic anhydride in ethanol was delivered. The N-acetylchitosan gel tube formed was washed with distilled water, and stored in a closed container containing sterile distilled water.

In another experiment, N-acetylchitosan fibers were made by starting from a solution of 6% chitosan (degree of acetylation 11%) in 2% aqueous acetic acid, which was diluted with an equal volume of methanol. The reaction mixture was filtered and degassed, and extruded through a single-hole spinneret (inner diameter 0.25 mm) into a bath containing 50% acetic anhydride in methanol. The N-acetylchitosan gel fiber formed was washed with distilled water, and air-dried resulting in an N-acetylchitosan fiber having a diameter of approximately 100 .mu.m.

2. Fabrication of Injectable Gels

A 3% solution of chitosan (degree of acetylation 11%) in 2% aqueous acetic acid was diluted with a twofold volume of ethanol. A 0.5 fold molar amount of acetic anhydride was added to the solution. The reaction mixture was sonicated to remove air-bubbles and transferred into a syringe. The resulting gel was extruded through a 30 gauge needle forming a gel-like extrudate.

3. Hydrolysis of N-acetylchitosan Gel Tubes

Figure 3:
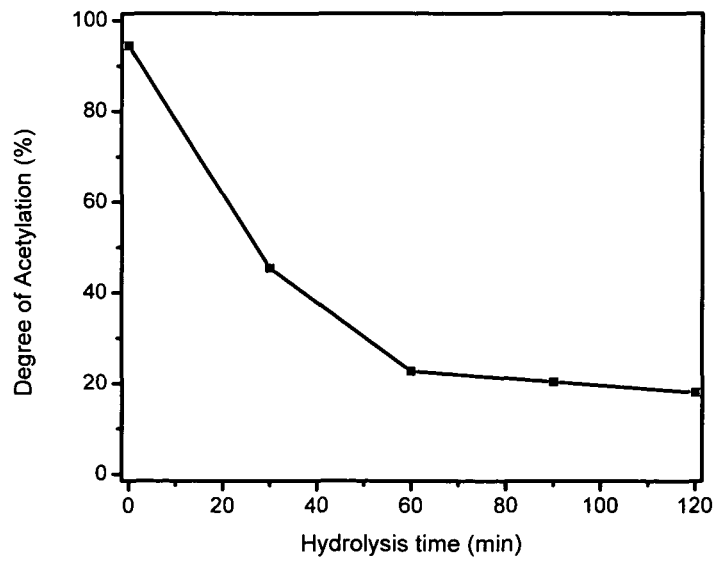
FIG. 3 illustrates the hydrolysis of N-acetylchitosan tubes with 40% aqueous sodium hydroxide solution at 110 .degree. C.
Figure 4:
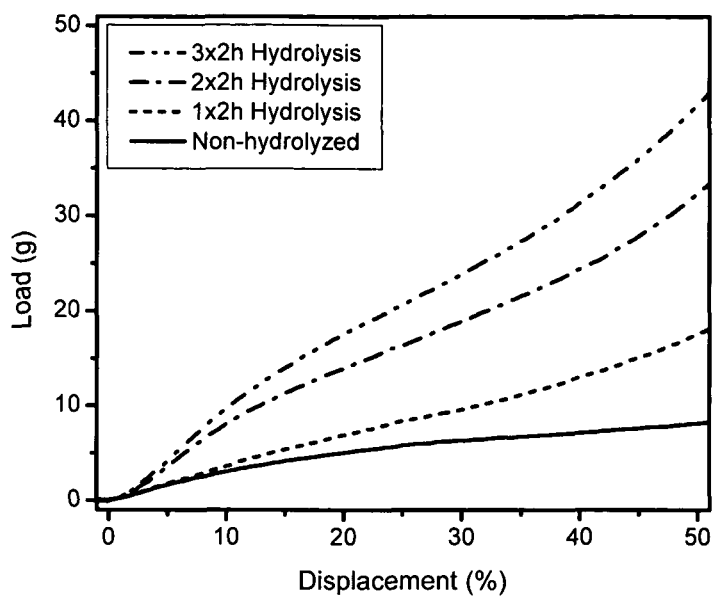
FIG. 4 illustrates typical load-displacement curves of N-acetylchitosan tubes (in phosphate buffered solution, 37.degree. C.) before and after one, two, or three hydrolysis cycles (for 2 h each) with 40% aqueous sodium hydroxide solution at 110.degree. C.

N-Acetylchitosan gel tubes were mounted on a cylindrical glass core (outer diameter 1.5 mm) and stored in a 40% aqueous solution of sodium hydroxide at 110.degree. C. for 2 h. The tubes were then intensely washed with distilled water, and air-dried for 3 h at room temperature and normal pressure. The degree of acetylation, as tested by NMR, decreased from 94% to 18% during hydrolysis (FIG. 3). To achieve greater levels of deacetylation, tubes were stored for 2 h in fresh alkaline solution as described above, followed by washing with water. This cycle of hydrolysis/washing was repeated up to 2 times. Degrees of acetylation of 3% and 1% were achieved after the second and third hydrolysis cycle. Hydrolysis resulted in tubes of high mechanical strength under physiological conditions (FIG. 4).

4. Drying of N-acetylchitosan Gel Tubes

Dried N-acetylchitosan tubes were fabricated by storing N-acetylchitosan gel tubes on air for 3 h at room temperature and normal pressure. A cylindrical glass core (diameter 1.5 mm), which was pre-coated with a thin layer of poly(.epsilon.-caprolactone) in order to facilitate subsequent tube removal, was inserted into the tubes during drying. Mechanical testing of tubes showed increased compression strength of dried tubes compared to hydrogels, despite smaller wall thicknesses, under physiological conditions (FIG. 5). Sterilization with ethylene oxide resulted in no significant changes in the compression strength.

In alternative experiments, small-diameter N-acetylchitosan tubes were fabricated by drying N-acetylchitosan gel tubes after mounting on platinum wire (diameter 125 .mu.m)

under conditions as described above, resulting in tubes with an inner diameter of 125 .mu.m. Similarly, platinum wire of 25 .mu.m has been used to fabricate tubes with an inner diameter of 25 .mu.m. Alternatively, stainless steel and copper have been used for tube fabrication.

5. Injection-molding of N-acetylchitosan Gel Fibers and Tubes

A 3% solution of chitosan (degree of acetylation 11%) in 2% aqueous acetic acid was diluted with an equal volume of ethanol and, after cooling to about 10.degree. C., mixed with a twofold molar excess of acetic anhydride. The reaction mixture was sonicated to remove air-bubbles and injected into a sealed cylindrical glass mold (inner diameter 0.8 mm). Gelation occurred within approximately 3 min and after 24 h, during which syneresis occurred, the N-acetylchitosan hydrogel fiber was removed from the mold and first washed with, and then stored in, water. Tubes were prepared in a similar manner, by using a cylindrical glass mold (inner diameter 4.0 mm), which contained a fixed central cylindrical glass core (diameter 1.7 mm).

6. Fabrication of Fiber Coils (FIG. 6)

N-Acetylchitosan gel fibers, fabricated as described in Example 1, were wound on a cylindrical mandrel, and the ends were fixed. After drying for 3 h at room temperature and normal pressure, the resulting shape-memorized N-acetylchitosan coil was re-immersed in water, removed from the mandrel, re-dried and stored in a closed container.

Figure 7:
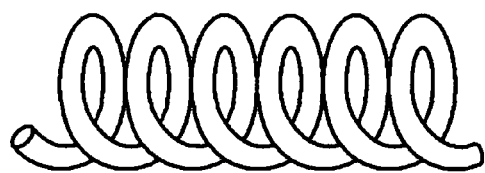
FIGS. 7 and 8 each is an illustration of another shaped medical device made from N-acylchitosan tube according to the present invention.

7. Fabrication of Hollow Fiber Coils (FIG. 7)

N-Acetylchitosan gel tubes were fabricated as described in Example 1. A cylindrical silicon core was inserted into the tube lumen. The tube/core assembling was wound on a cylindrical mandrel, and the ends were fixed. After drying for 3 h at room temperature and normal pressure, the resulting shape-memorized N-acetylchitosan coil was re-immersed in water, removed from the mandrel and the silicon core, and stored in distilled water. Similar results were obtained using platinum wire instead of silicon for insertion into the gel tube prior to winding and drying.

Figure 8:
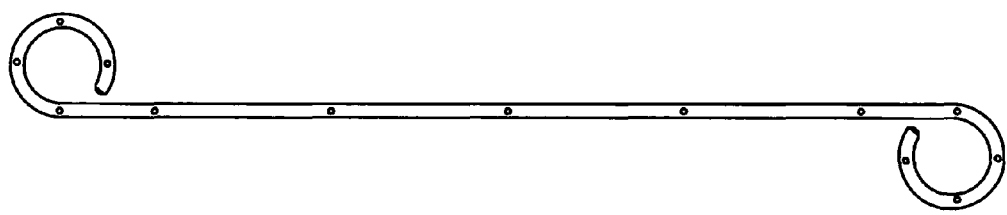

8. Fabrication of Ureteral Stents (FIG. 8)

N-Acetylchitosan gel tubes were fabricated as described in Example 1. A cylindrical silicon core was inserted into the tube lumen, and the ends of the tube/core assembling were fixed in a pigtail conformation. After drying for 3 h at room temperature and normal pressure, the resulting N-acetylchitosan ureteral stent having shape-memorized pigtail ends was re-immersed in water, removed from the silicon core, re-dried and stored in a closed container. Similar results were obtained using platinum wire instead of silicon for insertion into the gel tube prior to pigtail shape-fixation and drying. N-Acetylchitosan ureteral stents were further subjected to hydrolysis reactions. For this, the tube/core assembling fixed in a pigtail conformation and dried as described above was immersed in a 40% aqueous solution of sodium hydroxide at 110.degree. C. for 2 h. This step was repeated up to two times. The stent was washed intensely in distilled water, the silicon core removed, the stent dried and stored in a closed container. Similarly, platinum wire could be used for insertion into the N-acetylchitosan tube lumen during hydrolysis reactions.

Alternative experiments included hydrolysis of pigtail shape-fixed N-acetylchitosan gel tubes under conditions described above for dried tubes. In another alternative experiment, N-acetylchitosan gel tubes were hydrolyzed without any shape-fixation as described above. The tube ends were then fixed in pigtail conformation and dried similarly to the procedures described above.

In another experiment, N-acetylchitosan ureteral stents were coated with a polymer layer in order to adjust degradation times. For example, stents were dip-coated with a solution of poly(D,L-lactide-co-glycolide) in acetone. Preferable concentrations of the polymer solution were between 0.5% and 2%.

In yet another experiment, N-acetylchitosan ureteral stents were coated with a layer of barium sulfate, by dipping the stents into an aqueous suspension of barium sulfate, removal, and drying. Additionally, stents could be perforated, as illustrated in FIG. 8.

N-acetylchitosan ureteral stents have been tested for their biodegradation properties in vitro. In these experiments, stents were stored in human urine, which was replaced daily, at 37.degree. C. Results from these experiments are summarized in Table 1. Non-hydrolyzed stents showed stiffness and increasing brittleness including fragmentation into brittle pieces which would lead to discomfort in a patient. Stents hydrolyzed for 2 h in 40% aqueous sodium hydroxide at 110.degree. C. and coated with 0.5% PLGA showed a favourable degradation profile with respect to the target application: on day 3 the tube swelled and became soft; increasing softness was observed between days 3 and 9; beginning fragmentation into gel-like pieces at day 9; complete degradation at day 12. Such a degradation profile is highly desirable to allow for maximum functional efficacy and patient comfort during implantation and avoid a second surgical treatment. An advantage of stents hydrolyzed three times is their pH-dependent dissolution mechanism. These stents can be removed from the patients body in a highly controllable fashion, by adjusting the pH of the patient's urine, which can be done by treatment with basic or acidic compounds added to the diet. These methods of pH-adjustment of the urine are well-known in the clinical practice. For example, a basic pH may be maintained by giving a base or basic salt, such as acetazolamide or bicarbonate, to the patient for a desired period of time, e.g. 2 weeks, after which the urine may be made acidic (if not naturally back-regulated to an acidic pH) by giving an acid or acidic salt, such as ammonium chloride, which will, at a pH of less than about 6, result in a fast dissolution of the stent and its disappearance from the body. A general feature of all N-acetylchitosan modifications tested with respect to this invention is their inherent antibacterial potential which makes this class of materials highly promising for urological applications to prevent stent- or catheter-related infections.

TABLE-US-00001 TABLE 1 In vitro degradation/dissolution profile of N-acetylchitosan ureteral stents (urine, 37.degree. C.). N-Acetylchitosan Mechanical Properties ureteral stent Degradation Time during Degradation Non-hydrolyzed, 2 weeks increasing stiffness and non-coated brittleness Non-hydrolyzed, >10 weeks increasing stiffness and PLGA coated brittleness 1 .times. 2 h Hydrolysis, 3-5 days increasing softness and non-coated gel-like dissolution 1 .times. 2 h Hydrolysis, 10-12 days increasing softness and PLGA coated gel-like dissolution 3 .times. 2 h Hydrolysis, pH dependent stiffness essentially non-coated (2 days in acidic urine) unchanged, not brittle 3 .times. 2 h Hydrolysis, pH dependent stiffness essentially PLGA coated unchanged, not brittle

Figure 9A:
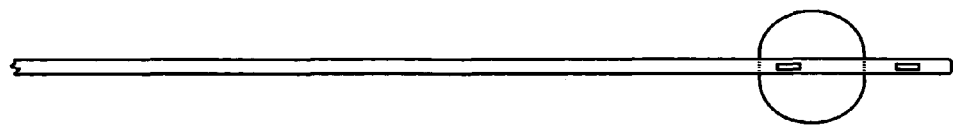
FIGS. 9A and 9B each is an illustration of a shaped medical device made from a combination of a two-channel tube and a hollow sphere according to the present invention.
Figure 9B:
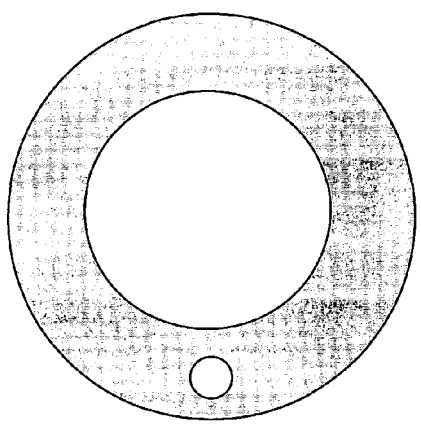

9. Fabrication of Foley Catheters (FIGS. 9A and 9B)

N-Acetylchitosan gel tubes were fabricated in a modified procedure to that described in Example 5, by injecting the acetylation reaction mixture into a cylindrical mold (inner diameter 5.5 mm), which contained two intraluminally fixed cylindrical cores (outer diameter 3.3 mm and 0.6 mm, respectively). Gelation and air-drying resulted in a two-channel N-acetylchitosan tube. The tubes were perforated, as illustrated in FIG. 9A. N-Acetylchitosan gel hollow spheres were fabricated by dipping an inflated polymeric balloon into the acetylation reaction mixture, removal from the mixture for gel formation on the outside of the inflated balloon, and air drying. The balloon was then deflated and removed from the formed hollow sphere, which was then mounted on the tube and fixed using a glue.

10. Coating of Coil-shaped Medical Devices (FIG. 10)

N-Acetylchitosan gel tubes were fabricated as described in Example 1. A helical coil was mounted on a cylindrical core, and the coil/core assembling was inserted into the tube. Air-drying of the gel resulted in the formation of a tubular N-acetylchitosan coating of the coil.

Figure 11:
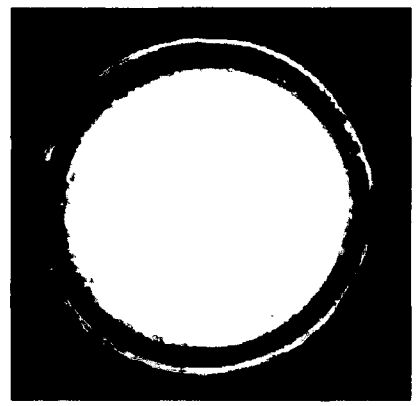
FIGS. 11 and 12 each is an image (cross-section) of a cylindrical medical device which is coated with N-acylchitosan according to the present invention.

11. Coating of Drug-Delivery Depots (FIG. 11)

N-Acetylchitosan gel tubes were fabricated as described in Example 1. A cylindrical drug pellet was inserted into the tube. Air-drying of the gel resulted in the formation of a tubular N-acetylchitosan coating of the pellet.

Figure 12:
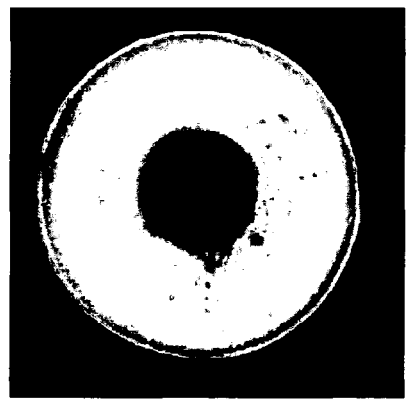

12. Coating of Medical Catheters (FIG. 12)

N-Acetylchitosan gel tubes were fabricated as described in Example 1. A catheter was inserted into the tube. Air-drying of the gel resulted in the formation of a tubular N-acetylchitosan coating of the catheter.

An alternative method, dipping of the catheter into the acetylation reaction mixture, removal for gel formation and air-drying of the gel formed on the surface of the catheter, has also been tested. The ends of the catheter have been closed with plugs prior to dipping to prevent intraluminal coating.

Figure 13:
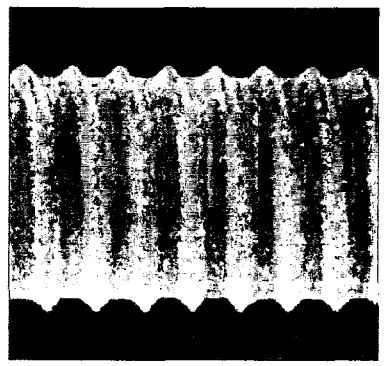
FIG. 13 is an image (side view) of a screw-shaped medical device which is coated with N-acylchitosan according to the present invention.

13. Coating of Medical Screws (FIG. 13)

N-Acetylchitosan gel tubes were fabricated as described in Example 1. A screw was inserted into the tube. Air-drying resulted in the formation of a corrugated N-acetylchitosan coating of the screw.

What is claimed is:

1. A process for manufacturing an article comprising N-acylchitosan hydrogel, the process comprising the steps of:
   providing a mixture comprising chitosan and/or N-acylchitosan; and
   injecting the mixture into a mold of pre-selected size and shape to form and shape the N-acylchitosan hydrogel.

2. The process of claim 1, wherein the mold is cylindrical.

3. The process of claim 2, wherein the mold comprises a centrally fixed core.

4. A process for manufacturing an article comprising N-acylchitosan, the process comprising the steps of:
   providing an N-acylchitosan hydrogel fixed in a desired shape; and
   at least partially drying the hydrogel, thereby forming an article with a memorized shape.

5. The process of claim 4, wherein the step of providing an N-acylchitosan hydrogel fixed in a desired shape comprises the steps of providing a mixture comprising chitosan and/or N-acylchitosan, and extruding the mixture to form an N-acylchitosan hydrogel.

6. The process of claim 5, wherein upon extrusion of the mixture, the N-acylchitosan hydrogel is formed essentially instantly.

7. The process of claim 5, wherein the mixture comprises a drug.

8. The process of claim 5, wherein the step of extruding the mixture comprises the extrusion of the mixture into a hydrogelation medium capable of promoting the formation of an N-acylchitosan hydrogel.

9. The process of claim 8, wherein the hydrogelation medium comprises an acylation agent.

10. The process of claim 8, wherein the hydrogelation medium further comprises a drug.

11. The process of claim 4, wherein the step of providing an N-acylchitosan hydrogel comprises the step of injecting or pouring a mixture comprising chitosan and/or N-acylchitosan into a mold.

12. The process of claim 4, wherein the mixture comprises chitosan or N-acylchitosan dissolved in a diluted acid and a cosolvent.

13. The process of claim 4, wherein the step of providing an N-acylchitosan hydrogel comprises coating another article with an N-acylchitosan hydrogel.

14. The process of claim 13, wherein the other article is a medical device.

15. The process of claim 13, wherein the other article comprises a drug.

16. The process of claim 4, wherein the mixture comprising chitosan and/or N-acylchitosan further comprises an acylation agent.

17. The process of claim 4, wherein the process further comprises, before the step of drying, at least one step of hydrolyzing to at least partially deacylate the N-acylchitosan.

18. The process of claim 4, further comprising the step of coating the article with at least one coating layer.

19. The process of claim 18, wherein the coating layer comprises a drug.

20. A process for manufacturing a tubular medical device, a stent, a catheter, a vascular graft, a nerve guide, a drainage tube, a fiber-based medical device, a suture, a medical device based on a mesh or a gauze, a wound dressing, or a tissue engineering scaffold, the process comprising the step of:
   forming an N-acylchitosan hydrogel.

* * * * *